US00PP19980P2

(12) United States Plant Patent
Jepsen

(10) Patent No.: US PP19,980 P2
(45) Date of Patent: May 12, 2009

(54) ***KALANCHOE* PLANT NAMED 'PURPLE JODIE'**

(50) Latin Name: ***Kalanchoe blossfeldiana*×*Kalanchoe laciniata***
Varietal Denomination: Purple Jodie

(75) Inventor: Knud Jepsen, Hinnerup (DK)

(73) Assignee: Knud Jepsen A/S, Hinnerup (DK)

( * ) Notice: Subject to any disclaimer, the term of this patent is extended or adjusted under 35 U.S.C. 154(b) by 0 days.

(21) Appl. No.: 12/006,220

(22) Filed: Dec. 31, 2007

(51) Int. Cl.
*A01H 5/00* (2006.01)

(52) U.S. Cl. ..... Plt./337; Plt./341

(58) Field of Classification Search ..... Plt./337, Plt./341

See application file for complete search history.

*Primary Examiner*—Annette H Para
*Assistant Examiner*—Louanne C Krawczewicz Myers
(74) *Attorney, Agent, or Firm*—C. A. Whealy

(57) ABSTRACT

A new and distinct cultivar of *Kalanchoe* plant named 'Purple Jodie', characterized by its compact, upright, uniform and moderately vigorous growth habit; medium-sized dark green-colored leaves; uniform and freely flowering habit; double light red purple-colored flowers; and excellent postproduction longevity.

1 Drawing Sheet

Botanical designation: *Kalanchoe blossfeldiana*×*Kalanchoe laciniata.*
Cultivar denomination: 'PURPLE JODIE'.

REFERENCED TO RELATED APPLICATIONS:

Title: *Kalanchoe Kalanchoe* Plant Named 'Dark Jodie'.
Applicant: Knud Jepsen.
Application Serial Number: Filed concurrently.

BACKGROUND OF THE INVENTION

The present invention relates to a new and distinct cultivar of *Kalanchoe* , botanically known as *Kalanchoe blossfeldiana*×*Kalanchoe laciniata,* and hereinafter referred to by the name 'Purple Jodie'.

The new *Kalanchoe* is a naturally-occurring whole plant mutation of the *Kalanchoe blossfeldiana*×*Kalanchoe laciniata* cultivar Jodie, disclosed in U.S. Plant Pat. No. 17,980. The cultivar Purple Jodie was discovered and selected by the Inventor as a flowering plant from within a population of plants of the cultivar Jodie in a controlled environment in Hinnerup, Denmark in April, 2006.

Asexual reproduction of the new *Kalanchoe* by vegetative terminal cuttings in a controlled environment in Hinnerup, Denmark since May, 2006, has shown that the unique features of this new *Kalanchoe* are stable and reproduced true to type in successive generations.

SUMMARY OF THE INVENTION

The cultivar Purple Jodie has not been observed under all possible environmental conditions. The phenotype may vary somewhat with variations in environment and cultural practices such as temperature, daylength and light intensity without, however, any variance in genotype.

The following traits have been repeatedly observed and are determined to be the unique characteristics of 'Purple Jodie'. These characteristics in combination distinguish 'Purple Jodie' as a new and distinct cultivar of *Kalanchoe* :

1. Compact, upright, uniform and moderately vigorous growth habit.
2. Medium-sized dark green-colored leaves.
3. Uniform and freely flowering habit.
4. Double light red purple-colored flowers.
5. Excellent postproduction longevity.

Plants of the new *Kalanchoe* can be compared to plants of the parent, the cultivar Jodie. Plants of the new *Kalanchoe* differ from plants of the cultivar Jodie in the following characteristics:

1. Plants of the new *Kalanchoe* are slightly shorter than plants of the cultivar Jodie.
2. Plants of the new *Kalanchoe* have narrower inflorescences than plants of the cultivar Jodie.
3. Plants of the new *Kalanchoe* have fewer petals per flower than plants of the cultivar Jodie.
4. Plants of the new *Kalanchoe* have slightly larger petals than plants of the cultivar Jodie.
5. Plants of the new *Kalanchoe* and the cultivar Jodie differ in flower color as plants of the cultivar Jodie have soft pink-colored flowers.

Plants of the new *Kalanchoe* can be compared to plants of the *Kalanchoe blossfeldiana*×*Kalanchoe laciniata* cultivar Dark Jodie, disclosed in U.S. Plant Pat. application Ser. No. 12/006,211. Plants of the new *Kalanchoe* differ from plants of the cultivar Dark Jodie in the following characteristics:

1. Plants of the new *Kalanchoe* are larger than plants of the cultivar Dark Jodie.
2. Plants of the new *Kalanchoe* flower about four days later than plants of the cultivar Dark Jodie.
3. Plants of the new *Kalanchoe* and the cultivar Dark Jodie differ in flower color.

Plants of the new *Kalanchoe* can be compared to plants of the *Kalanchoe blossfeldiana* cultivar Dark Cora, disclosed in U.S. Plant Pat. No. 13,938. In side-by-side comparisons conducted in Hinnerup, Denmark, plants of the new *Kalanchoe* differed from plants of the cultivar Dark Cora in the following characteristics:

1. Plants of the new *Kalanchoe* had slightly smaller flowers than plants of the cultivar Dark Cora.
2. Plants of the new *Kalanchoe* had double flowers whereas plants of the cultivar Dark Cora had single flowers.

BRIEF DESCRIPTION OF THE PHOTOGRAPHS

The accompanying colored photographs illustrate the overall appearance of the new *Kalanchoe* , showing the colors as true as it is reasonably possible to obtain in colored reproductions of this type. Colors in the photographs may differ slightly from the color values cited in the detailed botanical description which accurately describe the colors of the new *Kalanchoe* .

The photograph at the top of the sheet comprises a side perspective view of a typical flowering plant of 'Purple Jodie' grown in a container.

The photograph at the bottom of the sheet comprises close-up views of a typical inflorescence, upper and side perspective views of typical flowers, and typical vegetative and generative leaves of 'Purple Jodie'.

DETAILED BOTANICAL DESCRIPTION

The aforementioned photographs and following observations, measurements and values describe plants grown in Hinnerup, Denmark in a glass-covered greenhouse during the summer and under conditions which closely approximate commercial production. During the production of the plants, day temperatures were about 19° C. night temperatures were about 21° C. and light levels ranged from 10 kilolux to 50 kilolux. Unrooted cuttings were directly stuck in 10-cm containers and received long day/short night conditions (more than 14 hours of light) for about two weeks; plants then received photoinductive short day/long night conditions (minimum 14 hours darkness) until flowering. Plants were about twelve weeks old when the photographs and the description were taken. In the detailed description, color references are made to The Royal Horticultural Society Colour Chart, 2001 Edition, except where general terms of ordinary dictionary significance are used.

Botanical classification: *Kalanchoe blossfeldiana*× *Kalanchoe* laciniata cultivar Purple Jodie.

Parentage: Naturally-occurring whole plant mutation of the *Kalanchoe blossfeldiana*×*Kalanchoe laciniata* cultivar Jodie, disclosed in U.S. Plant Pat. No. 17,980.

Propagation:

*Type.*—By vegetative terminal cuttings.

*Time to initiate roots, summer.*—About two weeks at temperatures of 19° C. to 21° C.

*Time to initiate roots, winter.*—About three weeks at temperatures of 19° C. to 21° C.

*Time to produce a rooted young plant, summer.*—About three weeks at temperatures of 19° C. to 21° C.

*Time to produce a rooted young plant, winter.*—About 24 days at temperatures of 19° C. to 21° C.

*Root description.*—Fine, fibrous; white in color.

*Rooting habit.*—Freely branching; moderately dense.

Plant description:

*Plant habit.*—Compact, upright, uniform and moderately vigorous growth habit. Very freely flowering with numerous compound cymes. Inverted triangle with rounded crown. Moderately vigorous growth habit. Appropriate for 6-cm to 10-cm containers.

*Plant height at flowering.*—About 23 cm.

*Plant diameter at flowering.*—About 25 cm.

*Branching habit.*—Usually about eight to ten lateral branches develop per plant. Pinching (removal of the terminal apex) is not required but will enhance lateral branch development.

Lateral branch description:

*Length.*—About 12 cm to 16 cm.

*Diameter.*—About 6 mm.

*Internode length.*—About 2 cm to 6 cm.

*Aspect.*—Erect.

*Strength.*—Strong.

*Texture.*—Smooth, glabrous.

*Color.*—137A.

Foliage description:

*Arrangement.*—Opposite, simple; generally symmetrical.

*Length, vegetative plants.*—About 5 cm to 13 cm.

*Length, generative plants.*—About 6 cm to 9 cm.

*Length, generative plants.*—About 5 cm to 13 cm.

*Width, generative plants.*—About 2 cm to 9 cm.

*Shape.*—Ovate.

*Apex.*—Acute.

*Base.*—Obtuse.

*Margin.*—Crenate.

*Texture, upper and lower surfaces.*—Glabrous, leathery; succulent.

*Venation pattern.*—Pinnate.

*Color.*—Developing and fully expanded foliage, upper surface: 139A; towards the margins, 144A; venation, 139A. Developing and fully expanded foliage, lower surface: 138A; venation, 138A.

*Petiole.*—Length: About 0.5 cm to 3.5 cm. Diameter: About 5 mm to 7 mm. Texture, upper and lower surfaces: Smooth, glabrous. Color, upper and lower surfaces: 139A.

Flower description:

*Flower arrangement and habit.*—Double flowers arranged singly in compound dichasial cymes that arise from leaf axils. Uniform and freely flowering habit with usually about 15 to 35 flowers per inflorescence. Flowers not persistent. Flowers not fragrant.

*Natural flowering season.*—Plants of the new *Kalanchoe* initiate and develop flowers under short day/long night conditions or during the late autumn/winter/early spring. Flower initiation and development can also be induced under artificial short day/long night conditions (at least 14 hours of darkness).

*Time to flower.*—Under short day/long night photoinductive conditions, about 78 days are required. Actual time to flower is primarily dependent upon temperature and light intensity.

*Post-production longevity.*—Excellent post-production longevity; plants maintain good foliage and flower substance for about six weeks under interior environmental conditions.

*Inflorescence height.*—About 14 cm to 18 cm.

*Inflorescence diameter.*—About 3 cm to 5 cm.

*Flower diameter.*—About 2 cm to 2.3 cm.

*Flower length* (*height*).—About 5 mm.

*Flower bud.*—Shape: Lanceolate to ellipsoidal. Length: About 1.3 cm. Diameter: About 6 mm to 8 mm. Color: 144A and 69B tinted with N66B.

*Petals.*—Arrangement: About 18 to 30 fused at the base. Length (largest petals): About 1 cm. Width (largest petals): About 9 mm. Aspect: Slightly upright to eventually recurved. Shape: Broadly elliptic. Apex: Cuspidate. Margin: Entire. Texture, upper and lower surfaces: Smooth, glabrous. Color: When opening and fully opened, upper surface: N74A; color becoming closer to 74B with development. When opening and fully opened, lower surface: 69B and 144A tinted with N66B.

*Sepals.*—Appearance: Four fused at the base. Length: About 7 mm. Width: About 2 mm. Shape: Lanceolate. Apex: Acute. Base: Obtuse. Margin: Entire. Texture, upper and lower surfaces: Smooth; glabrous. Color, immature, upper and lower surfaces: 143A. Color, mature, upper surface: 143A. Color, mature, lower surface: 146A.

*Peduncles.*—Length: About 0.5 cm to 3 cm. Diameter: About 2 mm to 4 mm. Aspect: Erect to about 60° from vertical. Strength: Moderately strong to strong. Texture: Smooth, glabrous. Color: 144A.

*Pedicels.*—Length: About 1 mm to 4 mm. Diameter: About 1 mm. Aspect: Erect to about 90° from vertical. Strength: Strong. Texture: Smooth, glabrous. Color: 144A.

*Reproductive organs.*—Androecium: Stamen number: About four to six per flower. Anther shape: Elliptic. Anther size: About 1 mm by 1 mm. Anther color: Close to 20B. Amount of pollen: Scarce. Pollen color: Close to 20A. Gynoecium: Pistil number: About four per flower. Pistil length: About 3 mm. Style length: About 2 mm. Style color: 145A. Stigma shape: Round. Stigma color: 145C. Ovary color: Close to 138A.

*Seed.*—Quantity per flower: About 10 to 30. Length: Less than 1 mm. Diameter: Less than 1 mm. Color, immature: 145B. Color, mature: 177A.

Temperature tolerance: Plants of the new *Kalanchoe* have been observed to tolerate temperatures from about 5° C. to about 30° C.

Pathogen/pest resistance: Plants of the new *Kalanchoe* have not been observed to be resistant to pests and pathogens common to *Kalanchoe* .

It is claimed:

1. A new and distinct *Kalanchoe* plant named 'Purple Jodie' as illustrated and described.

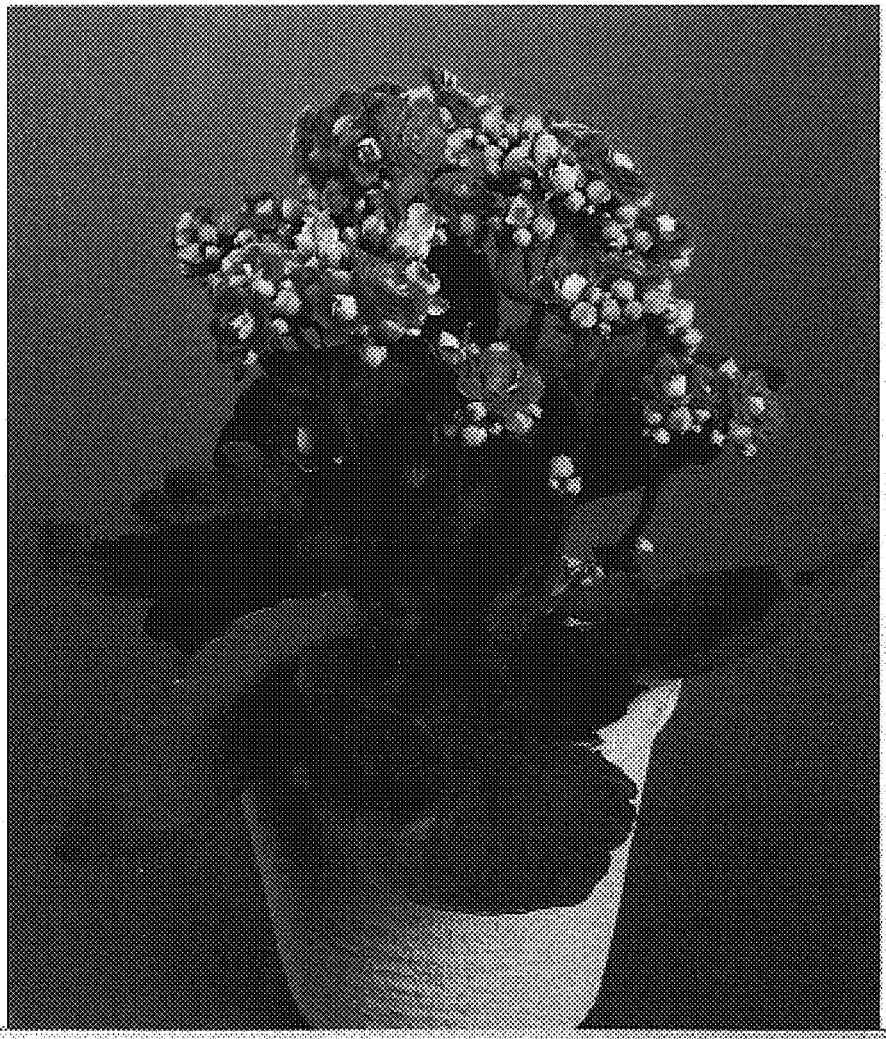
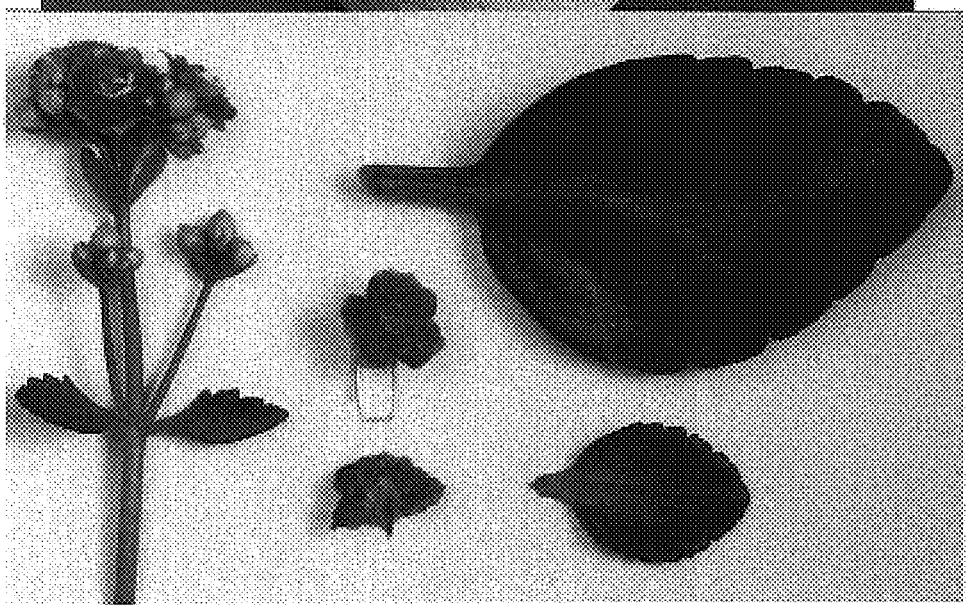

* * * * *